United States Patent
Lawandy

(10) Patent No.: US 9,789,069 B2
(45) Date of Patent: Oct. 17, 2017

(54) AUTHENTICATABLE COATINGS FOR PHARMACEUTICAL TABLETS AND INGESTIBLE MATERIALS

(71) Applicant: Spectra Systems Corporation, Providence, RI (US)

(72) Inventor: Nabil M. Lawandy, Saunderstown, RI (US)

(73) Assignee: Spectra Systems Corporation, Providence, RI (US)

( * ) Notice: Subject to any disclaimer, the term of this patent is extended or adjusted under 35 U.S.C. 154(b) by 696 days.

(21) Appl. No.: 13/630,895

(22) Filed: Sep. 28, 2012

(65) Prior Publication Data

US 2013/0084249 A1 Apr. 4, 2013

Related U.S. Application Data

(60) Provisional application No. 61/540,707, filed on Sep. 29, 2011.

(51) Int. Cl.
*A61K 9/44* (2006.01)
*A61K 9/28* (2006.01)
*A61J 3/00* (2006.01)
*A61K 9/20* (2006.01)

(52) U.S. Cl.
CPC ............. *A61K 9/2893* (2013.01); *A61J 3/005* (2013.01); *A61J 3/007* (2013.01); *A61K 9/2072* (2013.01); *A61K 9/2853* (2013.01); *A61K 9/2866* (2013.01); *A61J 2205/30* (2013.01); *A61J 2205/50* (2013.01)

(58) Field of Classification Search
None
See application file for complete search history.

(56) References Cited

U.S. PATENT DOCUMENTS

| 2002/0129523 | A1* | 9/2002 | Hunt | 40/594 |
|---|---|---|---|---|
| 2005/0267345 | A1* | 12/2005 | Korgel et al. | 600/317 |
| 2006/0159920 | A1* | 7/2006 | Reynders et al. | 428/402 |
| 2007/0160814 | A1* | 7/2007 | Mercolino | 428/195.1 |
| 2007/0190133 | A1* | 8/2007 | Bunick et al. | 424/464 |
| 2008/0019924 | A1* | 1/2008 | Kittler et al. | 424/10.2 |
| 2009/0116753 | A1* | 5/2009 | Midgley et al. | 382/219 |

\* cited by examiner

*Primary Examiner* — Robert A Wax
*Assistant Examiner* — Randeep Singh
(74) *Attorney, Agent, or Firm* — Barlow, Josephs & Holmes, Ltd.

(57) ABSTRACT

An authenticable and machine readable coating for pills, tablets and other ingestible materials is provided. The disclosure also relates to methods of authenticating the same. The coatings are formed from a lattice of particles stacked to cause selective diffraction such that each pill or tablet has an optical signature. The signature associated with each coating can be read and authenticated. In one embodiment, the particles are substantially spherical and self-organized. In one embodiment, generally recognized as safe (GRAS) materials are used to form the particles.

8 Claims, 3 Drawing Sheets

AUTHENTICATABLE COATINGS FOR PHARMACEUTICAL TABLETS AND INGESTIBLE MATERIALS

CROSS-REFERENCE TO RELATED APPLICATIONS

This application is related to and claims priority from earlier filed U.S. Provisional Patent Application No. 61/540,708, filed Sep. 29, 2011.

BACKGROUND OF THE INVENTION

The present invention relates generally to coatings for pills, tablets and other ingestible materials. More specifically, the present invention relates to an authenticable coating for pills, tablets and other ingestible materials that serves to identify the underlying material onto which the coating has been deposited as being genuine material.

With the widespread use of inexpensive modern technical advances comes the ability to duplicate, change, alter and distribute just about anything. Many law enforcement organizations have called counterfeiting the crime of the 21st century. Product counterfeiting is a serious and growing threat. Measures to defend against counterfeiters are being taken by many corporations, but they have not developed comprehensive, systematic, and cost-effective solutions to preventing counterfeiting. Due to advancing counterfeiting techniques, traditional anti-counterfeit technologies are becoming obsolete. Additionally, governments and corporations that have invested a great deal of resources in fighting counterfeiting have experienced little success. Furthermore, law enforcement agencies that are burdened with efforts to combat violent crimes have insufficient resources to fight counterfeiting crimes. For example, a company owning a famous brand name may have spent years developing and promoting the superior qualities of its goods to establish good will of the public and may be unable to stop a counterfeiter or a newcomer company product inferior quality goods.

Counterfeiting also extends to medical and pharmaceutical areas where counterfeiting can pose a serious threat and danger to public health. For example, goods such as oral pharmaceuticals encapsulated in tablets may be easily counterfeited. As the number of pharmaceutical compounds and drugs increases, efforts to develop brand affinity between competitors likewise increase. Typically, many drugs are sold as white or colored tablets formed by presses. These tablets are formed with a pattern, a number, a letter, shape or a combination in or on the surface of the tablet. These identifying features are intended to identify the source and sometimes the dosage. They are often hard to read, can be counterfeited, and do not reduce errors that occur at hospitals and pharmacies when filling prescriptions. Counterfeiting of this nature is particular adverse to the interests of original manufacturers of the drugs because this negatively impacts the sales of their products, but this also allows the wide and unsafe dissemination of dubious drugs. Consequently, both the public and the manufacturer face serious health and medical consequences and liability vis a vis the public because consumers may be sold counterfeit gray goods such as counterfeit drugs unbeknownst to them.

For example, one such difficulty lies in determining the origin of the drugs, particularly if the drugs themselves are not marked in such as way as to unequivocally determine their authenticity. This has often been the case with tablets. A problem is that although a package containing tablets may include a source designation code and other identifying brand or laboratory indicia, the tablet itself is not assigned such a code and may therefore be easily repackaged to hide its channel of distribution. Further, the absence of such a code or marking fails to assist in the identification of the distributor licensee that was responsible. Often tablet containers and packaging are properly marked and sealed so that the manufacturing source can be identified by some ID number. Since the container is sealed, one would expect that the tablets inside the container, for example, match the lot number on the container. Regrettably, as the cost of medication rises, the temptation grows for domestic and international manufacturers or suppliers to substitute some or all of the tablets of the container with a cheaper generic version or worse, inferior quality or counterfeit drugs, then seal the container, and pass it off as containing the tablets from the original name brand. It is likely that the consumer will not suspect the switch, although some may notice that the medication is less effective than expected. Regardless, the business profits handsomely. The manufacturer of the brand name product, however, in effect loses a sale and, worse, loses some of its good will as the consumer wrongfully blames the brand name manufacturer for the poor quality over which the manufacturer had no control. If the consumer suffers medically from the switched medication, the integrity of the brand name is damaged, not to mention the serious legal and product liability the manufacturer faces. In addition, the consumer does not get the brand name product for which he or she paid a premium. One reason this problem arises is because the consumer has no way of checking whether the tablets in the container are the proper tablets made by the labeled manufacturer.

To combat this problem, many approaches have been proposed for authenticating drugs and solid pharmaceutical goods, but none of these have proven entirely satisfactory. In particular, such proposed approaches do not provide an effective foolproof anti-piracy deterrent because many can be tampered with. For example, applying a bar code on the surface of a tablet can be easily tampered with. Such micro bar codes and administration of bar indicia on tablets, normal printing procedures such as roller rotation methods, ink-jet printing of tablets, are well known but not foolproof against forgeries and can be labor intensive to implement due to different porosity of pharmaceutical drugs, different quality of active ingredients of a tablet, the different thickness, absorption and smoothness of the tablets, the nonplanar small surface of the various types of different tablets, etc. This means that all these factors affect and influence the quality of the authentication and marking.

As a result, these previously known approaches do not provide adequate authentication and can often be defeated by clever tampering, copying, spoofing, or other advanced counterfeiting techniques. There is therefore a need for a coating material that is reliably authenticable yet difficult to copy or counterfeit. There is a further need for a coating that has a particular optical signature that can be authenticable for verification of genuine pharmaceutical materials. There is still further a need for a coating that has a particular optical signature that is machine readable to provide encoded information relating to the source, dosage and drug type.

BRIEF SUMMARY OF THE INVENTION

In this regard, the present invention provides a coating for pills, tablets and other ingestible materials that is authenticable and serves to identify the underlying material and its dosage onto which the coating has been deposited as being genuine material. As a result, the invention also relates to methods and devices for authenticating the coating and thus the material on which it is disposed.

The coatings disclosed herein are machine readable and can encode unique information that can be read to indicate the source, dosage, and drug type. The coatings are formed from a lattice of particles stacked to cause selective diffraction of light. Thus, each coating has an optical signature that can be read and authenticated.

In one embodiment, the particles are substantially spherical. The coating can include one or more layers of particles. In one embodiment, the stacking of the particles is configured to form a lattice. The lattice is sized to diffract light of different wavelengths into different angles. The particles used for the coating or substrate which is applied to an ingestible material are self-organized in one embodiment.

It is therefore an object of the present invention to provide a coating material that is reliably authenticable yet difficult to copy or counterfeit. It is a further object of the present invention to provide a coating that has a particular optical signature that can be authenticable for verification of genuine pharmaceutical materials. It is still a further object of the present invention to provide a coating that has a particular optical signature that is machine readable to provide encoded information relating to the source, dosage and drug type.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In the drawings which illustrate the best mode presently contemplated for carrying out the present invention.

DETAILED DESCRIPTION OF THE INVENTION

Figure 1:
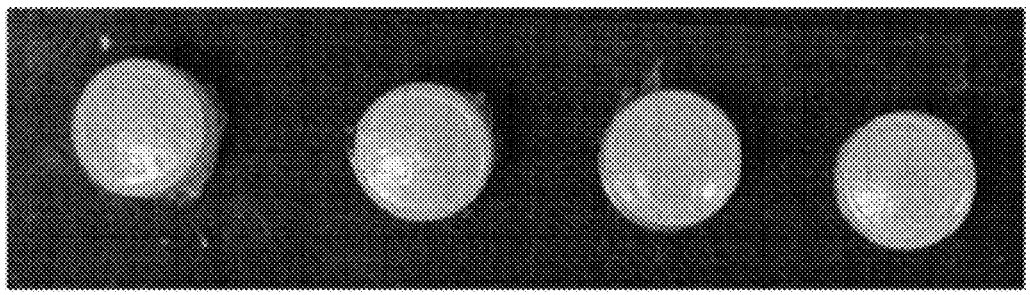
FIG. 1 is an image of tablets with the coating of the present invention thereon.

Now referring to the drawings, there is disclosed a coating for pills, tablets and other ingestible materials that is authenticable and serves to identify the underlying material onto which the coating has been deposited as being genuine material. As a result, the invention also relates to methods and devices for authenticating the coating and thus the material on which it is disposed.

The coatings disclosed herein are machine readable and can encode unique information that can be read to indicate the source, dosage, and drug type. The coatings are formed from a lattice of particles stacked to cause selective diffraction of light. Thus, each coating has an optical signature that can be read and authenticated. As can be seen at FIG. 1, this coating, results in both a distinct appearance to the user as well as a specific optical signature which can be controlled. The tablet or pill having a coating formed thereon as described below exhibits an opalescence or a pearlescent sheen which is distinct, visually appealing to a viewer and very difficult to replicate. In one embodiment, the coating causes a tablet or pill to look like a synthetic opal or pearl. The unique appearance is visually striking and different from conventional pill or tablet coatings.

The coatings can be formed by various nano-scale and micron scale materials. In one embodiment, the coating is formed from a layer or multiple layers of nano-particles. In one embodiment, the particles are self-organizing. For example, the particles can be spherical or substantially spherical in one embodiment. Further, as discussed below the particles can all be substantially the same size or have a common dimension, such as a diameter or layers of different sized particles can be used. Two images showing exemplary coatings formed from a plurality of particles are shown in FIGS. 2A and 2B.

Figure 2A:
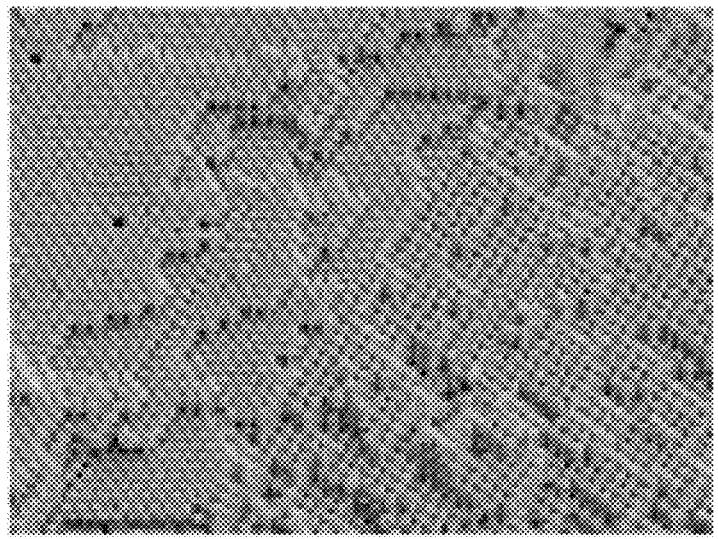
FIGS. 2A-B are magnified views of exemplary coatings firmed using a plurality of particles.
Figure 2B:
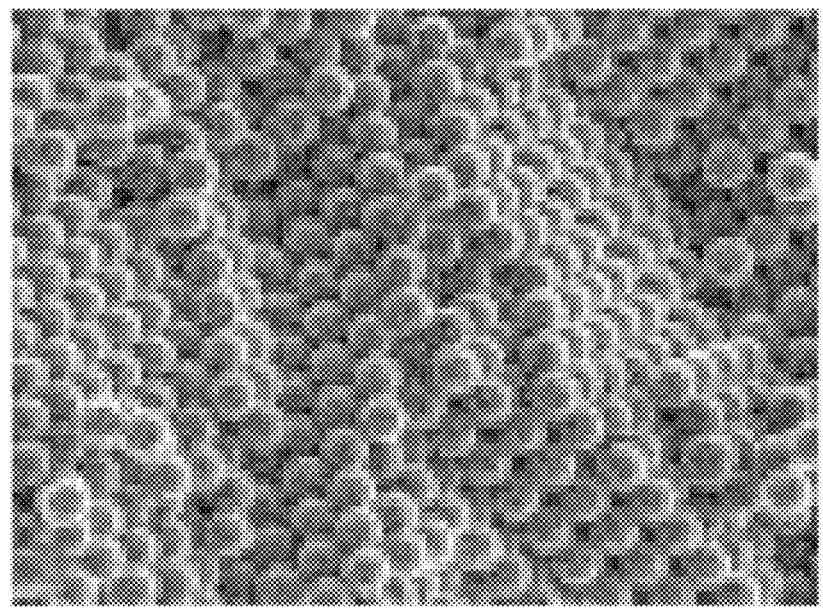

In particular, FIGS. 2A and 2B are electron microscopy images of an exemplary coating. The coating is authenticable and machine readable. FIG. 2B shows a magnified view of a region of the image of FIG. 2A. From both figures, a lattice or periodic structure that operates as a diffraction grating results from the close packing of the individual particles. The coatings are formed as a result of a self-organization and assembly process. The size and properties of the lattice pattern can be controlled and adjusted using this process. When illuminated with electromagnetic radiation, diffraction of light at specific wavelengths occurs at the coating. The spectral position of this diffraction is controlled through a built in periodicity on the scale of a fraction of the wavelength of visible light. Similar structures can be created with near infrared signatures using micron scale particles. Self-organization of the particles into a lattice occurs through evaporation of solvent and close-packing drives ordered states.

In one embodiment, the coatings include surface functionalized polystyrene nanospheres which are not generally recognized as safe (GRAS) materials. However, when producing these coatings to pills or other ingestible materials, GRAS nano-materials are used. In one embodiment, the GRAS materials can include, without limitation cross-linked polylactic acid and similar biopolymers. Other GRAS materials, can include, shellac, com protein, cellulose derivatives, and others. The coatings can be made using various materials and include multiple layers or only one layer of particles.

Figure 3:
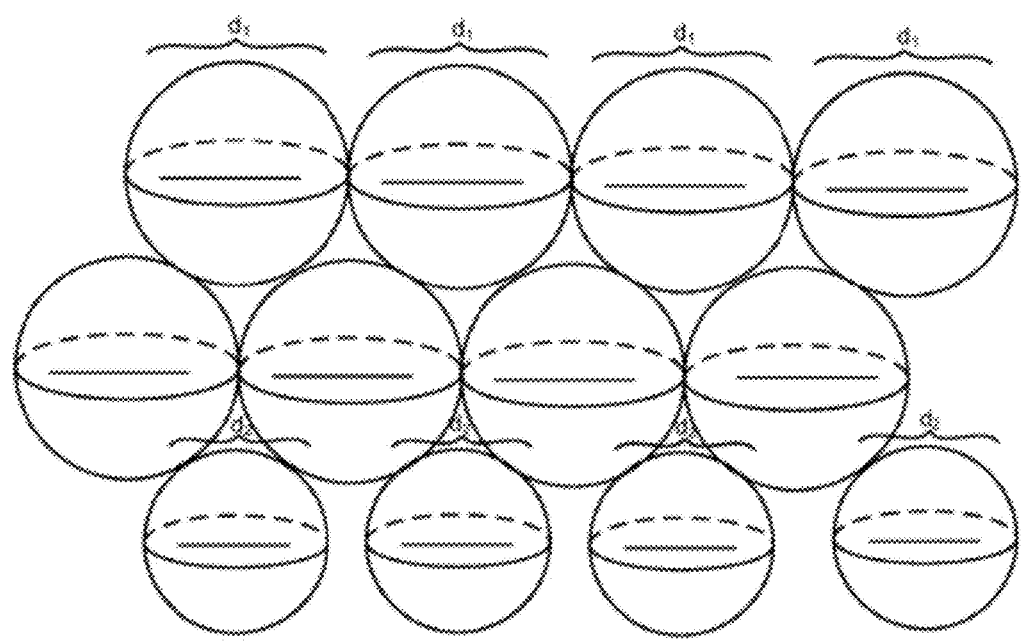
FIG. 3 is an exemplary coating formed from two layers of spherical particles.

An example of a coating for a pill tablet or other ingestible material that is formed from two layers of spherical particles is shown in FIG. 3. As shown, the coating includes a top layer that includes two layers of particles having a common dimension d1 and bottom layer that includes a single layer of particles having a common dimension d2 that is smaller than d1. In one embodiment, the stacking geometry of the spheres can be adjusted to tune the optical signature reflected from the coating. Different sized particles can also be mixed together so long as a lattice results that diffracts light in a desirable manner for coating authentication.

In one embodiment, the particles forming the coating can vary slightly in size, but are fabricated to remain within a particular size distribution. In one embodiment, the center to center particle distance or the particle diameter is the lattice spacing of a diffraction grating. Thus, the particle arrangement and size allows the lattice geometry to be tuned to selectively backscatter light. Thus, one dimension of the lattice is typically selected to be a fraction of a wavelength that will satisfy a Bragg scattering condition. In one embodiment, the coatings comprise a plurality of spherical particles having diameters which approximate a lattice spacing sized relative to a wavelength of light such that a Bragg scattering condition is satisfied. When electric magnetic radiation impinges on the coating, a reflective signal is propagated in the opposite direction that can be received processed by detector. In part, one embodiment of the invention is selectively tuning a lattice of spacing by changing the diameter or another dimension of the particles used to form the coating. This allows the optical signature for different coatings to be changed for different applications.

For example, a drug having three different dosages, can use three different coatings that incorporate particles sized to generate a different signal that is correlated with the three dosages. Multiple or nested coatings can be used to further modify the optical signature for the overall coating. Thus, a coating can include two layers of stacked particles with the particles in each layer having different sizes. In one embodiment, when light is shined on a double layer coating, two reflectivity spikes are detected. This allows various types of codes to be created by adjusting the peak and valley profile of the optical signature that is detected for a given coating when it is illuminated.

Figure 4:
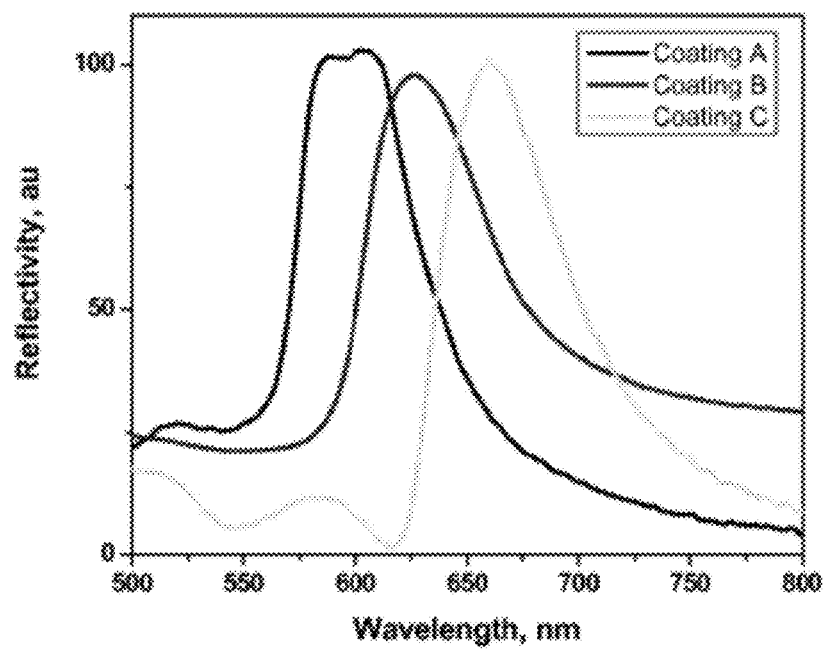
FIG. 4 is an illustration of multiple diffraction peaks resulting from a plurality of coatings.

By controlling the lattice spacing as well as the orientation of the Face Centered Cubic (FCC) crystal planes relative to the pill surface, a narrow band spectral diffraction peak can be covertly created. Accordingly, various geometric parameters can be adjusted to created different arrangements of diffraction peaks. White light illumination can be used when detecting an optical signature from a given coating in some embodiments. By using individual signatures as shown in FIG. 4 for the three different coatings shown, or by making combinations of different coatings, covert machine readable codes can be created. These unique codes can be stored in a database and associated with any number of parameters of interest. For example, the codes can be used to assure both authenticity of the product as well as the dosage of specific variants of the same compounds.

Figure 5:
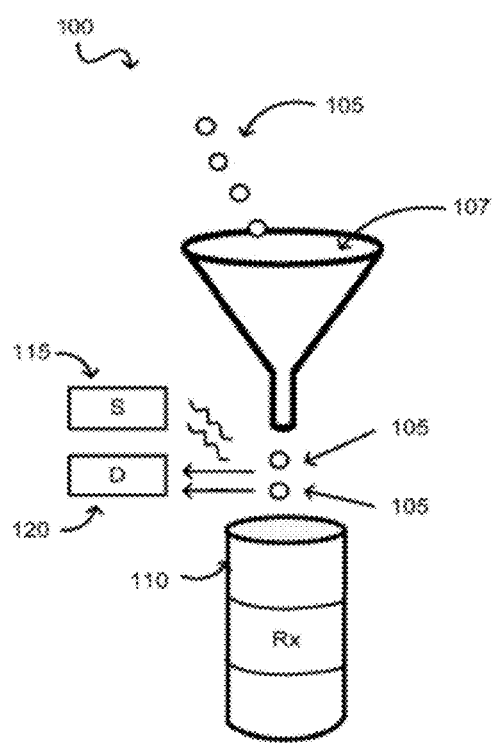
FIG. 5 is a depiction of a system for testing and authenticating coated materials in accordance with the present invention.

FIG. 5 depicts a system 100 suitable for use at a hospital, pharmacy, or manufacturing facility in which an ingestible material such as a pill 105 having a coating embodiment as described herein disposed thereon can be tested or authenticated. The pills 105 are be sorted using a sorter 107 such as a funnel or other pill 105 delivery device and deposited in a container 110 such as a prescription container. When each pill 105 is exposed to a source 115, which may be regular white light, a reader or detector 120 reads the optical signature that is scattered by the coating. These readers 120 are able to verify that the machine readable coating is authentic and also verify other information associated with the optical signature of the coating applied to each pill. Thus, before each prescription or load of pills 105 is stored in a container 110 the type of drug, its source, its dosage, expiration date, and other information can be verified. Further, given the optical nature of the signature and the detector, the process of scanning and verifying can happen very quickly such as on a real time basis.

It can therefore be seen that the present invention provides a coating material that is reliably authenticable yet difficult to copy or counterfeit. Further, the present invention provides a coating that has a particular optical signature that can be authenticable for verification of genuine pharmaceutical materials while being machine readable to provide encoded information relating to the source, dosage and drug type.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. A coating for an ingestible material comprising:
   a substrate;
   a first coating applied onto said substrate said coating having a first plurality of substantially spherical particles suspended therein, the particles having a first dimension that equals a fraction of a wavelength that will satisfy a Bragg scattering condition, wherein the particles self-arrange during application to define a plurality of lattices that selectively diffract electromagnetic radiation and wherein each of the plurality of particles comprise a generally recognized as safe material.

2. The coating of claim 1 wherein the first coating is opalescent or pearlescent.

3. The coating of claim 1 wherein the first dimension ranges from about 100 nm to about 2000 nm.

4. The coating of claim 1 wherein the substrate is a pill or tablet.

5. The coating of claim 1 wherein the first coating has a unique optical signature that is machine readable and authenticable using a detector.

6. The coating of claim 1 wherein the first plurality of particles is self-organized and defines one or more surfaces that selectively diffracts light.

7. The coating of claim 1 further comprising:
   a second coating disposed adjacent to the first coating, the second coating comprising a second plurality of particles, the particles having a second dimension, wherein the particles are stacked to define a plurality of lattices that selectively diffract electromagnetic radiation and wherein each of the second plurality of particles comprise a generally recognized as safe material.

8. The coating of claim 1 wherein the generally recognized as safe material is selected from the group consisting of cellulose and a cross-linked polylactic acid.

* * * * *